US008580309B2

(12) United States Patent  (10) Patent No.: US 8,580,309 B2
Wilson et al.  (45) Date of Patent: Nov. 12, 2013

(54) ANTIMICROBIAL MIXTURES

(75) Inventors: Michael Wilson, Southampton Row (GB); Ivan P. Parkin, Milton Keynes (GB); Sean Nair, London (GB)

(73) Assignee: UCL Business PLC, London (GB)

( * ) Notice: Subject to any disclaimer, the term of this patent is extended or adjusted under 35 U.S.C. 154(b) by 322 days.

(21) Appl. No.: 11/833,505

(22) Filed: Aug. 3, 2007

(65) Prior Publication Data

US 2008/0031960 A1  Feb. 7, 2008

Related U.S. Application Data

(60) Provisional application No. 60/821,423, filed on Aug. 4, 2006, provisional application No. 60/868,130, filed on Dec. 1, 2006.

(30) Foreign Application Priority Data

Jun. 22, 2007 (GB) .................................. 0712287.2

(51) Int. Cl.
  *A61K 9/14* (2006.01)
  *A61K 33/24* (2006.01)
  *A61K 31/54* (2006.01)
  *A61K 31/28* (2006.01)
  *A61K 31/5415* (2006.01)

(52) U.S. Cl.
  CPC ............... *A61K 31/5415* (2013.01); *A61K 9/14* (2013.01); *A61K 33/24* (2013.01); *A61K 31/28* (2013.01); *C01P 2004/64* (2013.01); *C10M 2219/108* (2013.01); *Y10S 977/777* (2013.01)
  USPC ........ 424/489; 424/649; 514/224.8; 514/495; 977/777

(58) Field of Classification Search
  None
  See application file for complete search history.

(56) References Cited

U.S. PATENT DOCUMENTS

| 5,830,526 | A | 11/1998 | Wilson et al. |
| 6,046,191 | A * | 4/2000 | Hamley et al. ............. 514/232.8 |
| 6,239,048 | B1 | 5/2001 | Wilson et al. |
| 6,420,455 | B1 | 7/2002 | Landgrebe et al. |
| 2002/0103517 | A1 | 8/2002 | West et al. |
| 2002/0119952 | A1 * | 8/2002 | Petrus ........................... 514/62 |
| 2003/0035750 | A1 | 2/2003 | Neuberger et al. |
| 2004/0077844 | A1 * | 4/2004 | Jacobson et al. .......... 530/391.5 |
| 2004/0192635 | A1 * | 9/2004 | Von Borstel et al. .......... 514/46 |
| 2005/0058713 | A1 * | 3/2005 | Russell et al. ................ 424/489 |
| 2005/0182152 | A1 | 8/2005 | Nonninger et al. |
| 2006/0159732 | A1 | 7/2006 | Cullen et al. |

FOREIGN PATENT DOCUMENTS

| GB | 0712287.2 | 7/2007 |
| KR | 2006024181 A * | 3/2006 |
| WO | WO 93/00815 | 1/1993 |
| WO | WO 99/49823 | 10/1999 |
| WO | WO 00/25940 | 5/2000 |
| WO | WO 03037297 | 5/2003 |
| WO | WO 0248432 | 6/2005 |
| WO | WO 2006-074117 | 7/2006 |
| WO | WO 2006-133271 A2 | 12/2006 |
| WO | WO 2007-023398 A2 | 3/2007 |

OTHER PUBLICATIONS

DC Hone, PI Walker, R Evans-Gowing, S FitzGerald, A Beeby, I Chambrier, MJ Cook, DA Russell. "Generation of Cytotoxic Singlet Oxygen via Phthalocyanine-Stabilized Gold Nanoparticles: A Potential Delivery Vehicle for Photodynamic Therapy." Langmuir 2002, 18, 2985-2987.*
W Tang, H Xu, R Kopelman, MA Philbert. "Photodynamic Characterization and In Vitro Application of Methylene Blue-containing Nanoparticle Platforms." Photochemistry and Photobiology, 2005, 81: 242-249.*
G Laurent, N Felidj, SL Troung, J Aubard, G Levi, JR Krenn, A Hohenau, A Leitner, FR Aussengg. "Imaging Surface Plasmon of Gold Nanoparticle Arrays by Far-Field Raman Scattering." Nano Letters, 2005, vol. 5 No. 2, pp. 253-258, Published on Web Dec. 24, 2004.*
G Frens. "Particle Size and Sol Stability in Metal Colloids." Kolloid-Z. u.Z. Polymere, 250, pp. 736-741, 1972.*
R Bhattacharya, P Mukherjee, Z Xiong, A Atala, S Soker, D Mukhopadhyay. "Gold Nanoparticles Inhibit VEGF165-Induced Proliferation of HUVEC Cells." Nano Letters, vol. 4 No. 12, 2004, pp. 2479-2481.*
Supporting Information for R Bhattacharya, P Mukherjee, Z Xiong, A Atala, S Soker, D Mukhopadhyay. "Gold Nanoparticles Inhibit VEGF165-Induced Proliferation of HUVEC Cells." Nano Letters, vol. 4 No. 12, 2004, pp. 2479-2481. This document is 3 pages, and the pages are not numbered.*
B Mayer, F Brunner, K Schmidt. "Inhibition of Nitric Oxide Synthesis by Methylene Blue." Biochemical Pharmacology, vol. 45, No. 2, 1993, pp. 367-374.*
JM Thomas. "Colloidal Metals: Past, Present, and Future." Pure and Applied Chemistry, vol. 60 No. 10, 1988, pp. 1517-1528.*
AR Peacocke, Sir C Hinshelwood. "The Absorption of Antibacterial Substances (2 : 8-Diaminoacridine and Methylene-blue) by Cells of Bact. lactis axogenes." J. Chem. Soc., 1948, pp. 2290-2303.*
Derwent Abstract of KR 2006024181. Original application published Mar. 16, 2006.*
N. Narband, S Tubby, IP Parkin, JG Tomans, D Ready, SP Nair, M Wilson. "Gold Nanoparticles Enhance the Toluidine Blue-Induced Lethal Photosensitisation of *Staphylococcus aureus*." Current Nanoscience, vol. 4, 2008, pp. 409-414.*
International Search Report PCT/GB2007/002957 Dated Nov. 30, 2007.
Duncan C. Hone, Peter I. Walker, Richard Evans-Gowing, Simon Fitzgerald, Andrew Beeby, Isabelle Chambrier, Michael J Cook and David A. Russell, *Langmuir*, 2002, 18, 2985-7.

(Continued)

*Primary Examiner* — Frederick Krass
*Assistant Examiner* — Isaac Shomer
(74) *Attorney, Agent, or Firm* — Hoxie & Associates LLC

(57) ABSTRACT

The present invention presents a mixture comprising charge-stabilized metallic nanoparticles and a photosensitizer, a method for making such mixture, and a method of using such mixture for killing or preventing the growth of microbes.

8 Claims, 2 Drawing Sheets

(56) References Cited

OTHER PUBLICATIONS

Brust, M; Walker, M; Bethell, D; Schiffrin, D J; Whyman, R; *J. Chem. Soc. Chem. Comm*, 1994, 801-802.
Simpson, T R E; Revell, D J; Cook, M J; Russell, D A; *Langmuir*, 1997, 13, 460-464.
Revell, D J; Chambrier, I; Cook, M J; Russell, D A; *J. Mater Chem*, 2000, 10, 31-37.

Marie-Christine Daniel and Didier Astruc, *Chem. Rev.* 2004, 104, 293-346.
Wieder et al, "Intracellular photodynarnic therapy with photosensitizer nanoparticle conjugates", Photochem. Photobiol. Sci., 2006, 5, 727-734.
Yang et al, "Photosensitizer decorated iron oxide nanoparticles", Proc. of SPIE, 2006, 6139, 613906-1-603906-10.

* cited by examiner

☐ viable count of the original bacterial suspension
▦ viable count of the bacterial suspension after exposure to white light alone
▨ incubation in the dark with TBO
☰ incubation in the dark with the TBO-tiopronin-gold nanoparticle conjugate
▦ TBO + white light
■ TBO-tiopronin-gold nanoparticle conjugate + white light ☐ viable count of the original bacterial suspension
▨ viable count of the bacterial suspension after exposure to HeNe laser light for 1 minute
▨ incubation in the dark with TBO
▤ incubation in the dark with the TBO-tiopronin-gold nanoparticle conjugate
▨ TBO + HeNe laser light
■ TBO-tiopronin-gold nanoparticle conjugate + HeNe laser light

US 8,580,309 B2

ANTIMICROBIAL MIXTURES

CLAIM OF BENEFIT OF FILING DATE

This application claims the benefit of U.S. Provisional Patent Application Ser. No. 60/821,423 titled: "Antimicrobial Mixtures" filed on Aug. 4, 2006, U.S. Provisional Patent Application Ser. No. 60/868,130 titled: "Antimicrobial Conjugates" filed on Dec. 1, 2006, and United Kingdom Patent Application No. 0712287.2 titled: "Antimicrobial Conjugates" filed on Jun. 22, 2007.

FIELD OF INVENTION

The present invention relates to mixtures comprising charge-stabilized metallic nanoparticles and a photosensitiser, and their use as light activated antimicrobials. The present invention also relates to metallic nanoparticle-ligand-photosensitiser conjugates and their use as light activated antimicrobials.

BACKGROUND OF THE INVENTION

Photosensitisers, such as toluidine blue O, act as light-activated antimicrobial agents. Although they may have no antimicrobial activity at low concentrations in the dark, when irradiated with light of a certain wavelength (such as 633 nm for toluidine blue O) they are able to kill a wide range of microbes. Killing is thought to be due to the singlet oxygen produced on irradiation of the compound. There is considerable interest in enhancing the activity of existing photosensitisers. The present invention focuses on one method of achieving this.

US 2005/0058713 describes that singlet oxygen production by a photosensitiser (zinc phthalocyanine) is enhanced by covalently linking it to gold nanoparticles (see also Duncan C. Hone, Peter I. Walker, Richard Evans-Gowing, Simon FitzGerald, Andrew Beeby, Isabelle Chambrier, Michael J. Cook, and David A. Russell. Langmuir 2002, 18, 2985-7). However, this increase in singlet oxygen generation has been reported to be due, at least in part, to the presence of tetraoctylammonium bromide—a reagent used in the preparation of the phthalocyanine-nanogold. The authors concluded, therefore, that the singlet oxygen generating system was, in fact, a three-component system consisting of nanogold, the phthalocyanine and the tetraoctylammonium bromide. Although the phthalocyanine/nanogold/tetraoctylammonium bromide was found to increase singlet oxygen generation, it was not demonstrated that these particles were able to kill either mammalian cells or microbes.

Nanoparticle suspensions are inherently unstable, and the nanoparticles tend to associate, or clump together. Two methods are used to counter this. One is ligand-stabilization, which is employed, for example, in US 2005/0058713. The other is charge-stabilization.

The present inventors have found that, surprisingly, simple mixing of charge-stabilized metallic nanoparticles with a photosensitiser results in enhancement of antimicrobial activity.

The present inventors have also found that, surprisingly, metallic nanoparticle-ligand-photosensitiser conjugates, in which a photosensitiser is directly bound, via the ligand, to ligand-stabilised nanoparticles, have enhanced antimicrobial properties.

SUMMARY OF THE INVENTION

In one aspect of the invention there is provided a mixture comprising charge-stabilized metallic nanoparticles and a photosensitiser. The invention also provides a process for preparing such a mixture.

In another aspect, the present invention provides use of the mixtures as antimicrobials.

In yet another aspect, the present invention provides use of the mixtures in the manufacture of a medicament for killing or preventing the growth of microbes.

The present invention also provides a process of killing or preventing the growth of microbes, comprising using the mixtures of the present invention.

In another aspect, the present invention provides use of a metallic nanoparticle-ligand-photosensitiser conjugate, wherein: the ligand is a water-solubilising ligand; and the metallic nanoparticle and photosensitiser are chosen such that the conjugate generates singlet oxygen and/or free radicals as a light-activated antimicrobial.

In one aspect, the use as an antimicrobial is for inanimate objects and surfaces.

In another aspect, the present invention provides the above-mentioned conjugates for use in killing or preventing the growth of microbes or for ameliorating or reducing the incidence of proliferative cell disorders such as cancer in the human or animal body.

The present invention also provides new metallic nanoparticle-ligand-photosensitiser conjugates, comprising gold, tiopronin and toluidine blue, and a process for making these and other conjugates useful in the present invention. Photodisinfection can meet the need to treat infections and decolonize microbes residing in body cavities without the use of antibiotics.

DESCRIPTION OF THE PREFERRED EMBODIMENT

I. Nanoparticle-Photosensitiser Mixtures

Figure 1:
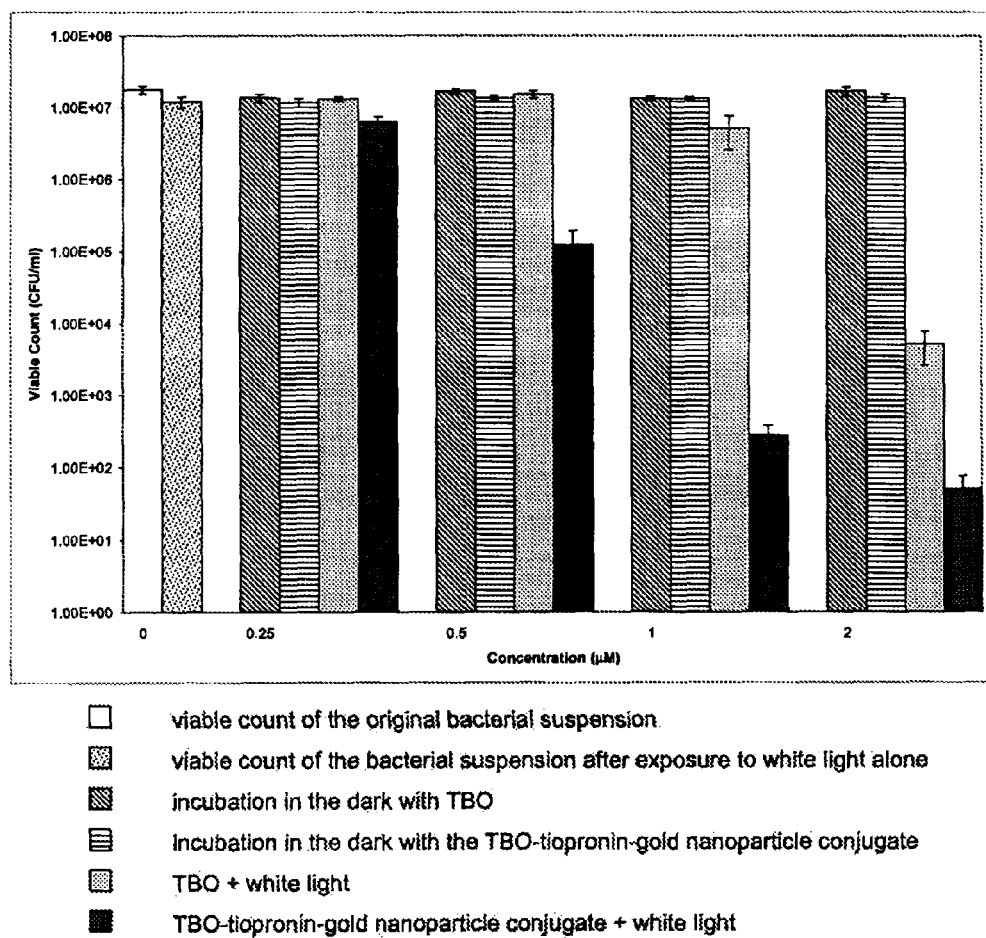
FIG. 1 shows the effect of TBO and the TBO-tiopronin-gold nanoparticle conjugate on viability of Staphylococcus aureus 6571 following exposure to white light for 30 minutes or incubation in the dark with TBO or the TBO-tiopronin-gold nanoparticle conjugate.

The term "nanoparticles" is generally understood to mean particles having a diameter of from about 1 to about 100 nm. Preferably, the nanoparticles used in the present invention have a diameter of from about 1 to about 30 nm. In one embodiment, the nanoparticles preferably have a diameter of from about 2 to about 5 nm. In another embodiment, the nanoparticles preferably have a diameter of from about 10 to about 25 nm, more preferably about 15 to about 20 nm.

Nanoparticles typically, but not exclusively, comprise metals. They may also comprise alloys of two or more metals, or more complex structures such as core-shell particles, rods, stars, spheres or sheets. A core-shell particle may typically comprise a core of one substance, such as a metal or metal oxide or silica, surrounded by a shell of another substance, such as a metal, metal oxide or metal selenide. The term "metallic" as used herein is intended to encompass all such structures having a metallic outer surface.

In a preferred embodiment, the outer surface of the metallic nanoparticles of the present invention comprises a main group metal or transition metal, such as cobalt. More preferably, the metallic nanoparticles are gold, silver or copper nanoparticles, or alloys of two or more of these metals. Most preferably, the nanoparticles are gold nanoparticles.

A photosensitiser is a compound that can be excited by light of a specific wavelength. Thus, such a compound may have an absorption band in the ultraviolet, visible or infrared portion of the electromagnetic spectrum and, when the compound absorbs radiation within that band, it generates cytotoxic species, thereby exerting an antimicrobial effect. The effect may be due to creation of singlet oxygen but the invention is not limited to photosensitisers that exhibit antimicrobial effects through creation of singlet oxygen.

Without wishing to be bound by theory, it is thought that the photosensitiser and nanoparticles are associated via dative covalent bonds, wherein the electrons are provided by, for example, S or N moieties on the photosensitiser.

Any photosensitiser may be used in the present invention. However, it is preferable that the photosensitiser is non-toxic to humans and animals at the concentrations employed in the present invention. It is also preferable that the photosensitiser demonstrates antimicrobial activity when exposed to visible light. The photosensitiser is suitably chosen from porphyrins (e.g. haematoporphyrin derivatives, deuteroporphyrin), phthalocyanines (e.g. zinc, silicon and aluminium phthalocyanines), chlorins (e.g. tin chlorin e6, poly-lysine derivatives of tin chlorin e6, m-tetrahydroxyphenyl chlorin, benzoporphyrin derivatives, tin etiopurpurin), bacteriochlorins, phenothiaziniums (e.g. toluidine blue O, methylene blue, dimethylmethylene blue), phenazines (e.g. neutral red), acridines (e.g. acriflavine, proflavin, acridine orange, aminacrine), texaphyrins, cyanines (e.g. merocyanine 540), anthracycline (e.g. adriamycin and epirubicin), pheophorbides, sapphyrins, fullerene, halogenated xanthenes (e.g. rose bengal), perylenequinonoid pigments (e.g. hypericin, hypocrellin), gilvocarcins, terthiophenes, benzophenanthridines, psoralens and riboflavin. Other possibilities are arianor steel blue, tryptan blue, crystal violet, azure blue cert, azure B chloride, azure 2, azure A chloride, azure B tetrafluoroborate, thionin, azure A eosinate, azure B eosinate, azure mix sicc. and azure II eosinate.

In one embodiment, particularly preferred photosensitisers are toluidine blue O, methylene blue, dihaematoporphyrin ester, tin chlorin e6, indocyanine green or nile blue sulphate. More preferably, the photosensitiser is toluidine blue O, methylene blue or tin chlorin e6. Most preferably, the photosensitiser is methylene blue or toluidine blue O.

In a particularly preferred embodiment, the mixture comprises gold nanoparticles and methylene blue or toluidine blue O.

A. Process for Preparation of the Mixtures

In one embodiment, the mixtures of the present invention are in the form of a solution. Such a solution may be produced by contacting a solution of charge-stabilized metallic nanoparticles with a solution of photosensitiser. The mixtures are contacted at any suitable temperature, for example between the freezing point and boiling point of the solvent employed (or at a temperature at which both solutions are liquid if different solvents are employed). However, if the temperature is too high, the nanoparticle solution may become unstable. It is preferred that the nanoparticle solution remains in a stable condition. In one embodiment, the solutions are contacted at or about room temperature.

In one embodiment, a solution of metallic nanoparticles is mixed with a solution of photosensitiser and allowed to stand at room temperature for at least about 10 minutes, preferably between about 10 minutes and about 1 hour, more preferably between about 15 and about 20 minutes.

Typically, the metallic nanoparticle solution and/or the photosensitiser solution is a solution in a polar solvent, preferably an aqueous solution, such as in water or phosphate buffered saline solution, in particular in a pharmaceutically acceptable aqueous carrier. More preferably, both the nanoparticle and photosensitiser solutions are aqueous.

The pH of solutions may be such that no adjustment is required upon mixing, or the pH of the mixture may be controlled by the use of a suitable buffer. For example, when the mixture is to be applied to the body, the pH of the mixture should not be outside the physiological pH range for the site. The physiological pH range depends on the site in question, e.g. intact skin can have a pH as low as 4.2.

The two solutions may be mixed in any proportion, such that the desired concentration is achieved in the mixed solution. In one embodiment, the initial concentrations of each solution are selected as required so that the desired concentration in the mixed solution is achieved when equal volumes of metallic nanoparticle solution and photosensitiser solution are mixed together.

The desired concentration of the nanoparticles in the mixture depends on the desired final concentration at the site to be treated. This may vary and a suitable choice depends both on the size of the nanoparticle and the concentration of the photosensitiser solution. The final concentration of the nanoparticles in the mixture is preferably from about $1 \times 10^{11}$ to about $5 \times 10^{15}$ particles/ml, more preferably from about $3 \times 10^{11}$ to about $1 \times 10^{15}$ particles/ml. In order to obtain such a final concentration, the initial concentration of the nanoparticle solution is typically from about $1 \times 10^{12}$ to about $1 \times 10^{15}$ particles/ml. If the nanoparticle solution as prepared, or as obtained commercially, is of higher concentration than this, it may be necessary to dilute the nanoparticle solution before mixing with the photosensitiser. For example, an original nanoparticle solution containing $1 \times 10^{14}$ or $1 \times 10^{15}$ particles/ml may be diluted 1:10 to 1:100, such that the concentration before mixing with the photosensitiser solution is from $1 \times 10^{12}$ to $1 \times 10^{14}$.

The initial concentration of photosensitiser solution is preferably chosen such that when mixed with the nanoparticle solution, the final concentration of photosensitiser at the treatment site is from about 5 to about 100 μM, more preferably from about 20 to about 50 μM.

It should be noted that the final concentration at the treatment site may not necessarily correspond to the concentration in the mixed solution. For instance in the treatment of periodontal pockets and wounds the treatment site may be flooded with body fluid such as saliva or blood. In such cases, it may therefore be necessary to apply the nanoparticle-photosensitiser mixture in greater concentration so as to achieve an effective concentration after dilution by the body fluid.

B. Antimicrobial Effect of the Mixtures

The mixtures of the present invention have an antimicrobial effect, i.e. they are capable of killing or inhibiting the growth of microorganisms, including bacteria, viruses, fungi and prions, that can cause disease in humans, animals or plants. In one embodiment, the mixtures of the present invention are used to kill or inhibit the growth of *Staphylococcus aureus*. *Staphylococcus aureus* as used in this application shall also include Methicillin-Resistant *Staphylococcus aureus* ("MRSA"). The mixtures of the present invention may also be used to kill or inhibit the growth of *Propionibacterium acnes*.

In another embodiment, the mixtures of the present invention are used to kill or prevent the growth of the microbes involved in oral diseases, such as inflammatory periodontal disease and caries, or in wound infections and in disinfecting or sterilising wounds and other lesions in the oral cavity. Thus, the mixtures of the present invention may be used to kill or inhibit the growth of *Streptococcus sanguis, Porphyromonas gingivalis, Fusobacterium nulceatum, Actinobacillus actinomycetemcomitans, Candida albicans, Streptococcus mutans* and lactobacilli.

The antimicrobial effect of the mixtures is activated by exposure to a light source. In one embodiment, the mixture may be exposed to a light source comprising radiation having a wavelength, or a range of wavelengths, within the range of wavelengths absorbed by the photosensitiser, preferably near or corresponding to the wavelength of maximum absorption of the photosensitiser ($\lambda_{max}$). As described above, it is preferred that the photosensitiser demonstrates antimicrobial activity when exposed to visible light, i.e. $\lambda_{max}$ is between about 380 and about 780 nm. For example, toluidine blue O demonstrates antimicrobial activity when irradiated with light having a wavelength of 633 nm.

In general, any light source that emits light of an appropriate wavelength may be used. The source of light may be any device or biological system able to generate monochromatic or polychromatic light, coherent or incoherent light, especially visible white light. Examples include a fluorescent light source, laser, light emitting diode, arc lamp, halogen lamp, incandescent lamp or an emitter of bioluminescence or chemiluminescence. In certain circumstances, sunlight may be suitable. Preferably, the wavelength of the light emitted by the light source may be from about 200 to about 1060 nm, preferably from about 380 to about 780 nm. A suitable laser may have a power of from about 1 to about 100 W. Other suitable lasers may have a power of about 1 to about 1000 mW and a beam diameter of from about 1 to about 10 mm. The light dose for laser irradiation is suitably from about 5 to about 333 J cm$^{-2}$, preferably from about 5 to about 30 J cm$^{-2}$ for laser light. For white light irradiation, a suitable dose is from about 0.01 to about 100 J/cm$^2$, preferably from about 0.1 to about 20 J/cm$^2$, more preferably from about 3 to about 10 J/cm$^2$. In a preferred embodiment, the mixture may suitably be irradiated using a source of white light.

Without limitations, the following are examples of light sources and their respective exemplary wavelengths and/or power outputs that may be suitable for use in the present invention:

Helium neon (HeNe) gas laser (e.g. 633 nm)
Argon-pumped dye laser (e.g. 500-700 nm, 5 W output)
Copper vapour-pumped dye laser (e.g. 600-800 nm)
Excimer-pumped dye laser (e.g. 400-700 nm)
Gold vapour laser (e.g. 628 nm, 10 W output)
Tunable solid state laser (e.g. 532-1060 nm), including Sd:YAG
Light emitting diode (LED) (e.g. 400-800 nm)
Diode laser (e.g. 630-850 nm, 25 W output), e.g. gallium selenium arsenide
Tungsten filament lamp
Halogen cold light source
Fluorescent lamp (e.g. 10 to 30 W)

The present invention is not limited to the above-mentioned examples of light sources, exemplary wavelengths and/or power outputs. It is entirely possible for the present invention to be carried out using other light sources and/or the above-mentioned light sources with different wavelengths and/or power outputs.

The duration of exposure to the light source should be long enough to ensure sufficient killing. This may vary depending on the choice of photosensitiser and light source. For example, toluidine blue O may require exposure for between 10 and 30 minutes to ensure effective killing of microbes using a 15 to 30 W fluorescent lamp, but only 20 to 60 seconds using a fibre optic white light source. Other photosensitisers, such as tin chlorin e6, may require 10 to 30 minutes with a fibre optic white light source. In one embodiment, the duration of irradiation is suitably from about one second to about 15 minutes, preferably from about 1 to about 5 minutes. In another embodiment, for example when the light source is of low intensity such as exposure to natural daylight, the mixture is exposed to the light source for a longer period of time, such as for several hours, for example from about 1 to about 12 hours.

The light may be delivered to the mixture by ambient exposure, or, if necessary or convenient, by use of a directed means such as a fibre optic light source or other known optical devices.

The efficacy of the mixtures as antimicrobials depends on many factors. The choice of nanoparticle type, choice of photosensitiser, nanoparticle size, concentration of nanoparticles and concentration of photosensitiser may all influence antimicrobial activity. Thus individual combinations may have particularly advantageous effects. For example and without limitations, the following combinations have been found particularly effective against *Staphylococcus aureus*:

2 nm diameter gold nanoparticles at a concentration of $4\times10^{13}$ particles/ml with toluidine blue O at a concentration of 20 µM.

15 nm diameter gold nanoparticles at a concentration of $1\times10^{14}$ to $1\times10^{15}$ particles/ml with toluidine blue O at a concentration of 20 to 50 µM.

2 nm diameter gold nanoparticles at a concentration of $4\times10^{11}$ to $4\times10^{13}$ particles/ml with methylene blue at a concentration of 20 µM.

15 nm diameter gold nanoparticles at a concentration of $1\times10^{13}$ to $1\times10^{15}$ particles/ml with methylene blue at a concentration of 20 µM.

2 nm diameter gold nanoparticles at a concentration of $4\times10^{11}$ particles/ml with tin chlorin e6 at a concentration of 20 µg/ml.

2 nm gold nanoparticles at a concentration of $4\times10^{13}$ particles/ml with nile blue sulphate at a concentration of 20 to 50 µM.

C. Applications of Mixtures

The antimicrobial properties of the mixtures of the present invention may find application in hospitals and other places where microbiological cleanliness is necessary, for example food processing facilities, dining areas or play areas. Use in abattoirs is also envisaged. The mixtures may be applied to any suitable surface in order to sterilize it, for example work surfaces, wash basins, toilets, tiles, door handles or computer keyboards. In another embodiment, the mixture may be applied to cling-film or other films or packaging, such as food packaging, for example by spraying or painting a solution of the mixture onto the film. Such cling-film type material could be wrapped around or used to cover medical/dental instruments, computer input devices, surfaces etc.

The mixtures may be applied as a coating by painting, spreading or spraying and may be dried or allowed to dry naturally. They can also be mixed with a plastics material such as cellulose acetate to create an antimicrobial plastic.

Such a plastics material could be used to manufacture articles, such as computer input devices, or as antimicrobial coverings to be wrapped or coated over the surface of the article to be treated. Thus, in one embodiment, an article such as a computer input device could be coated with a mixture of cellulose acetate, photosensitiser and nanoparticles.

In another embodiment, the antimicrobial properties of the mixtures of the present invention may find application in killing the microbes involved in oral diseases, as mentioned above. The mixtures of the present invention may also find use in killing or preventing the growth of microbes in various body cavities. Body cavity shall mean any cavity within a body such as mouth or oral cavity, nose, ear, vagina, lung, the entire digestive tract (e.g., throat, esophagus, stomach, intestines, rectum, etc.), gall bladder, bladder, any open wound or the like. The body cavity can be within a human body or a body of another animal.

The mixtures of the present invention may also be applied topically, for example to the skin, wounds or a mucosal surface in order to kill or prevent the growth of microbes. As a further example, the mixtures of the present invention may find application in killing or preventing the growth of fungi, for example in infections of the nail bed.

For such applications, the mixture is suitably in the form of a solution or a suspension in a pharmaceutically acceptable aqueous carrier, but may be in the form of a solid such as a powder or a gel, an ointment or a cream. The composition may be applied to the infected area by painting, spreading, spraying, injecting or any other conventional technique.

The present invention also provides use of a mixture of the present invention in the manufacture of a medicament for killing or preventing the growth of microbes, and a method of disinfecting or sterilising a locus in subject, which method comprises the administration to the said locus of an effective amount of a mixture of the present invention followed by exposure of said locus to a light source.

In a preferred aspect the invention provides the use of a mixture of the present invention in the manufacture of a medicament for use in disinfecting or sterilising tissues of a body cavity or a wound or lesion in a body cavity by (a) contacting the tissues, wound or lesion with mixture and (b) irradiating the tissues, wound or lesion with light at a wavelength absorbed by the photosensitiser.

The wound or lesion treated may be any surgical or trauma-induced wound, a lesion caused by a disease-related microbe, or a wound or lesion infected with such a microbe. The treatment may be applied to disinfect or sterilise a wound or lesion as a routine precaution against infection or as a specific treatment of an already diagnosed infection of a wound or lesion. In one embodiment, the body cavity is the oral cavity. The mixtures of the present invention may also be used in other body cavities, such as the nose, rectum, vagina, etc.

In another preferred aspect the invention provides the use of a mixture of the present invention in the manufacture of a medicament for use in killing or preventing the growth of disease-related microbes in a body cavity, such as the oral cavity, nose, rectum, vagina, etc. by (a) contacting the microbes with mixture and (b) irradiating the microbes with light at a wavelength absorbed by the photosensitiser.

When the body cavity is the oral cavity, the treatment with mixture and irradiation are preferably applied to (i) destruction of disease-related microbes in a periodontal pocket in order to treat chronic periodontitis; (ii) destruction of disease-related microbes in the region between the tooth and gingiva (gingival crevice or gingival margin) in order to treat or prevent inflammatory periodontal diseases, including chronic periodontitis, gingivitis and the like; (iii) disinfection or sterilisation of drilled-out carious lesions prior to filling; (iv) destruction of cariogenic microbes on a tooth surface in order to prevent dental caries; (v) disinfection or sterilisation of dental and/or gingival tissues in other dental surgical procedures and (vi) treatment of oral candidiasis in AIDS patients, immunocompromised patients or patients with denture stomatitis.

For the above applications, the mixture is suitably used in the form of a pharmaceutical composition comprising the nanoparticles and photosensitiser in solution in a pharmaceutically acceptable aqueous carrier. The pharmaceutical composition may further comprise one or more accessory ingredients selected from buffers, salts for adjusting the tonicity of the solution, antioxidants, preservatives, gelling agents and remineralisation agents.

In another aspect, the present invention provides a process of killing or preventing the growth of microbes, comprising contacting with a mixture according the present invention followed by exposure to a light source for a sufficient amount of time to kill or prevent the growth of microbes. As described above, the mixture is at a suitable concentration such that a desired level of antimicrobial activity is achieved at the treatment site. Thus, the "final concentrations" as described above are preferred. For application to surfaces, the mixture may be applied directly by any suitable means, such as a cloth, spray or wash. For oral or topical applications, any of the methods mentioned above, i.e. painting, spreading, spraying, injecting or any other conventional technique, may be used to contact the mixture with the microbes.

The mixture may be left in contact with the microbes for a period of time. This duration of time may vary depending on the particular photosensitiser in use and the target microbes to be killed. For example, it can be from about 1 second to about 10 minutes. In one embodiment, the duration of time is about 10 seconds to about 2 minutes. In another embodiment, the duration of time is about 30 seconds.

In one aspect, the present invention does not extend to the use of the mixtures in methods of treatment of the human or animal body by surgery or therapy, or in methods of diagnosis conducted on the human or animal body.

II. Metallic Nanoparticle-Ligand-Photosensitiser Conjugates

The term "nanoparticle" is generally understood to mean particles having a diameter of from about 1 to about 100 nm. Preferably, the nanoparticles used in the present invention have a diameter of from about 1 to about 30 nm, preferably about 1 to about 20 nm.

Nanoparticles typically, but not exclusively, comprise metals. They may also comprise alloys of two or more metals, or more complex structures such as core-shell particles, rods, stars, spheres or sheets. A core-shell particle may typically comprise a core of one substance, such as a metal or metal oxide or silica, surrounded by a shell of another substance, such as a metal, metal oxide or metal selenide. The term "metallic" as used herein is intended to encompass all such structures having a metallic outer surface.

The metallic nanoparticles of the present invention should be chosen such that, when attached via the ligand to the photosensitiser to form the conjugate, the conjugate generates singlet oxygen and/or free radicals. Preferably, the conjugate generates both singlet oxygen and free radicals.

Singlet oxygen generation may be measured by assay: several such methods are known to those skilled in the art, for example, photoluminescence. Free radical generation may be measured using electron proton resonance (EPR).

Examples of metallic nanoparticles that may be suitable are nanoparticles having a diameter of greater than about 2 nm which exhibit plasmon resonance in the wavelength band of about 200 to about 1600 nm, i.e. covering the visible to near infrared bands. The plasmon resonance may be measured by UV spectroscopy. It may be seen for both the free and conjugated nanoparticle. For antimicrobial applications, preferable nanoparticles will exhibit plasmon resonance at wavelengths of from about 500 to about 600 nm. Gold nanoparticles, for example, exhibit plasmon resonance in this range.

Another property which may be used to help select a suitable nanoparticle is the molar extinction coefficient of the conjugated photosensitiser. When a photosensitiser is conjugated via a ligand to a suitable nanoparticle, the extinction coefficient of the photosensitiser may be enhanced, compared to the extinction coefficient that would be expected based on an equivalent concentration of the photosensitiser alone. Without wishing to be bound by theory, it is thought that this enhancement occurs because the photosensitiser coordinates to the surface of the nanoparticle. Thus, in order to select suitable nanoparticles, the extinction coefficient of the conjugate could be measured, using a spectrophotometer. Any enhancement is acceptable. Typically, the extinction coefficient may range anywhere from about 2 to about 30 times or more; from about 5 to about 30 times or more; from about 10 to about 30 times or more and from about 20 to about 30 times or more, compared to what is expected based on the same concentration of the unconjugated photosensitiser.

In a preferred embodiment, the outer surface of the nanoparticles of the present invention comprises gold, silver or copper. More preferably, the nanoparticles comprise gold, silver or copper, or alloys of two or more of these metals, such as gold/silver, gold/copper or gold/silver/copper. Suitable alloys may also contain other metals, such as gold/silver/aluminium.

In another embodiment, the nanoparticles described in the preceding paragraph comprise core-shell particles. It is possible for such core-shell particles to comprise a magnetic core or magnetic layer. An example of such a magnetic core-shell particle is a particle having a magnetic core and an outer shell which comprises gold. Most preferably, the nanoparticles are gold nanoparticles.

The ligand of the metallic nanoparticle-ligand-photosensitiser conjugate is desired to be a water-solubilising ligand. This means that the conjugate as a whole is water soluble at a concentration of at least about $1\times10^{-8}$ M (mol dm$^{-3}$) at room temperature (25° C.). Preferably, the conjugate is water soluble at a concentration of at least about $1\times10^{-7}$ M, more preferably at least about $1\times10^{-6}$ M.

The concentration for determining water solubility may be measured by any appropriate method. Suitable methods include UV absorption, inductively coupled plasma mass spectrometry (ICP-MS), SQUID (superconducting quantum interference device) magnetometry, EPR or Raman spectroscopy.

Examples of suitable ligands are water-solubilising ligands chosen from sulfur ligands, such as thiols (alkanethiols and aromatic thiols), xanthates, disulfides, dithiols, trithiols, thioethers, polythioethers, tetradentate thioethers, thioaldehydes, thioketones, thion acids, thion esters, thioamides, thioacyl halides, sulfoxides, sulfenic acids, sulfenyl halides, isothiocyanates, isothioureas or dithiocarbamates; selenium ligands, such as selenols (aliphatic or aromatic), selenides, diselenides, dialkyl-diselenides (for example octaneselenol-nanoparticle is obtained from dioctyl-diselenide), selenoxides, selenic acids or selenyl halides; tellurium ligands, such as tellurols (aliphatic or aromatic), tellurides or ditellurides; phosphorus ligands, such as phosphines or phosphine oxides; nitrogen ligands, such as alkanolamines or aminoacids; and other ligands such as carboxylate ligands (e.g. myristate), isocyanide, acetone and iodine.

Examples of preferred water-solubilising ligands are 3-mercaptopropionic acid, 4-mercaptobutyric acid, 3-mercapto-1,2-propanediol, cysteine, methionine, thiomalate, 2-mercaptobenzoic acid, 3-mercaptobenzoic acid, 4-mercaptobenzoic acid, tiopronin, selenomethionine, 1-thio-beta-D-glucose, glutathione and ITCAE pentapeptide.

A photosensitiser is a compound that can be excited by light of a specific wavelength. Thus, such a compound may have an absorption band in the ultraviolet, visible or infrared portion of the electromagnetic spectrum and, when the compound absorbs radiation within that band, it generates cytotoxic species, thereby exerting an antimicrobial effect. The effect may be due to creation of singlet oxygen but the invention is not limited to photosensitisers that exhibit antimicrobial effects through creation of singlet oxygen. In particular, the photosensitiser may generate free radicals, instead of, or as well as, generating singlet oxygen.

It is a requirement of the present invention that the photosensitiser is chosen such that, when attached to the metallic nanoparticle-ligand core to form the conjugate, the conjugate generates singlet oxygen and/or free radicals. Preferably, the conjugated photosensitiser generates both singlet oxygen and free radicals. Singlet oxygen and free radical generation may be measured as described above.

It is preferable that the photosensitiser is non-toxic to humans and animals at the concentrations employed in the present invention. It is also preferable that the photosensitiser demonstrates antimicrobial activity when exposed to visible light. The photosensitiser is suitably chosen from porphyrins (e.g. haematoporphyrin derivatives, deuteroporphyrin), phthalocyanines (e.g. zinc, silicon and aluminium phthalocyanines), chlorins (e.g. tin chlorin e6, poly-lysine derivatives of tin chlorin e6, m-tetrahydroxyphenyl chlorin, benzoporphyrin derivatives, tin etiopurpurin), bacteriochlorins, phenothiaziniums (e.g. toluidine blue O, methylene blue, dimethylmethylene blue), phenazines (e.g. neutral red), acridines (e.g. acriflavine, proflavin, acridine orange, aminacrine), texaphyrins, cyanines (e.g. merocyanine 540), anthracyclins (e.g. adriamycin and epirubicin), pheophorbides, sapphyrins, fullerene, halogenated xanthenes (e.g. rose bengal), perylenequinonoid pigments (e.g. hypericin, hypocrellin), gilvocarcins, terthiophenes, benzophenanthridines, psoralens and riboflavin. Other possibilities are indocyanine green, nile blue sulphate, arianor steel blue, tryptan blue, crystal violet, azure blue cert, azure B chloride, azure 2, azure A chloride, azure B tetrafluoroborate, thionin, azure A eosinate, azure B eosinate, azure mix sicc. and azure II eosinate.

In one embodiment, particularly preferred photosensitisers are toluidine blue O (TBO), methylene blue, tin chlorin e6, indocyanine green or nile blue sulphate. Preferably, the photosensitiser is not a porphyrin. More preferably, the photosensitiser is toluidine blue O, methylene blue or tin chlorin e6. Most preferably, the photosensitiser is methylene blue or TBO.

The proportion of metallic nanoparticle:ligand:photosensitiser may vary. Typically, the nanoparticle comprises many atoms, only some of which have ligand molecules covalently bonded thereto. The number of photosensitiser molecules attached to each nanoparticle-ligand core may also vary. Typically, only some of the ligand molecules will have a photosensitiser molecule attached. For example, a preferred conjugate according to the present invention could have the composition $Au_{201}Tiopronin_{85}TBO_9$, $Au_{201}Tiopronin_{85}TBO_{11}$ or $Au_{201}Tiopronin_{85}TBO_{15}$.

The conjugate may also comprise further components. For example, it may have a targeting moiety associated with it. The targeting moiety can be associated with the conjugate via any suitable means, for example it may be attached to the nanoparticle core, to the ligand or to the photosensitiser. Such targeting moieties may be suitable, for example, for targeting specific microorganisms, or for targeting cancer cells. For example, they may be antibodies with specificity for the target organism or cancer cell. Other examples of targeting moieties include bacteriophages, protein A (targets *Staphylococcus aureus*) and bacterial cell-wall binding proteins or peptides.

The preferred conjugate mentioned above is an example of another aspect of the present invention. Thus the present invention also provides novel metallic nanoparticle-ligand-photosensitiser conjugates, wherein the metallic nanoparticle comprises gold, the ligand comprises tiopronin and the photosensitiser comprises (TBO). In one embodiment, the novel conjugate preferably consists of gold-tiopronin-TBO. Preferably, the novel conjugate comprises from about 5 to about 20 TBO groups per nanoparticle-ligand core.

The novel conjugates of the present invention have been found to demonstrate particularly effective antimicrobial properties. Thus all uses of conjugates as described herein apply to the novel conjugates.

A. Process for Preparation of the Conjugates

The present invention provides a process for producing conjugates as described above. Such a process comprises the steps of:
(i) providing a nanoparticle-ligand core, comprising a nanoparticle having bonded thereto at least one ligand having first and second functional groups, wherein the ligand is bonded to the nanoparticle via the first functional group, and then
(ii) reacting the second functional group of at least one of said ligands with a functional group of a photosensitiser.

Preferred nanoparticles, ligands and photosensitisers for use in the process of the present invention are as described above. Preferably, both steps of the process are carried out in aqueous solution.

One embodiment of the process will now be illustrated by reference to the novel gold-tiopronin-TBO conjugates described above.

Typically, the nanoparticle-ligand core is prepared by a reaction based on the Brust reaction (Brust, M; Walker, M; Bethell, D; Schiffrin, D J; Whyman, R; J. Chem. Soc. Chem. Comm., 1994, 801-802). Such reactions are well known to those skilled in the art. However, in the case of a gold-tiopronin core, it is preferable to modify the usual reaction mixture, and the reaction is preferably executed in a methanol/acetic acid mixture, rather than in toluene. Furthermore, the amount of acetic acid should be controlled such that a final pH of about 5 is achieved after addition of sodium tetrahydroborate.

The nanoparticle-ligand core is preferably purified, for example by dialysis, before reaction with the photosensitiser.

Typically, the reaction between the nanoparticle-ligand core and photosensitiser takes place in an aqueous medium. In one embodiment, a catalyst can be used. For example, 1-[3-(dimethylamino)-propyl]-3]ethyl-carbodiimide (EDC) can be used to catalyse reactions between tiopronin carboxylic acid groups and an aromatic amine-containing TBO molecule. N-hydroxysulfosuccinimide sodium salt may be included in the reaction mixture to improve the efficiency of the reaction.

Typically, the reaction feed ratio of photosensitiser to nanoparticle-ligand core is such that it provides from about 0.5 to about 2 functional groups on the photosensitiser per "second functional group" on the ligand. Preferably, the ratio is about 1:1. Such a ratio provides conjugates with from about 5 to about 20 molecules of photosensitiser per core, as described above.

Conjugates prepared by a process according to the present invention are typically stable, showing no decomposition over a period of months.

B. Conjugate Compositions

Compositions comprising a conjugate for use in the present invention typically comprise a solution or suspension of the conjugate in a suitable solvent, such as water or phosphate buffer solution. As described above, the conjugate as a whole is water soluble at a concentration of at least about $1\times10^{-8}$ M (mol dm$^{-3}$). However, at concentrations above this lower limit, it is not necessary that the conjugate is completely soluble in water. The conjugate may form a suspension in water, or may be dissolved to form a solution in a medium with a higher dielectric constant, such as saline or phosphate buffered saline (PBS). Gold-tiopronin-TBO conjugates, for example, may be suspended in water, but are soluble in PBS: the water solubility is determined by the TBO content, with lower TBO amounts leading to greater water-solubility of the conjugates.

Suitable concentrations of conjugate in a suspension/solution may be calculated based on the amount of photosensitiser present. Thus, for example a TBO-containing conjugate could be used such that the final TBO content is between about 0.01 and about 1 μM, preferably from about 0.1 to about 0.5 μM. In another embodiment, the final TBO content is preferably from about 0.25 to about 5 μM, preferably from about 0.5 to about 2 μM. The final desired concentration of photosensitiser should be such that the composition has antimicrobial activity when exposed to a light source, as described further below. The actual concentration will depend on many factors, including the type of photosensitiser, the light source to be used and the duration of exposure. However, without wishing to be bound by theory, it can be generally stated that if the concentration of photosensitiser is too low, antimicrobial activity may not be seen due to insufficient generation of singlet oxygen and/or free radicals, and if the concentration is too high, light penetration into the solution or suspension may be compromised. In the latter case, any antimicrobial effect will be suppressed due to failure of much of the composition to become "light activated".

It should be noted that the final concentration of conjugate at a site to be disinfected may not necessarily correspond to the concentration in the solution/suspension. For instance in the treatment of periodontal pockets and wounds the treatment site may be flooded with body fluid such as saliva or blood. It may therefore be necessary to apply the conjugate composition in greater concentration so as to achieve an effective concentration after dilution by other fluids, such as body fluid and the like.

The pH of solutions may be such that no adjustment is required, or the pH of the composition may be controlled by the use of a suitable buffer. For example, when the composition is to be applied to the body, the pH of the composition is preferably not outside the physiological pH range for the site. The physiological pH range depends on the site in question, e.g. intact skin can have a pH as low as about 4.2 (Microbial inhabitants of humans: their ecology and role in health and disease. Wilson M (2005) Cambridge University Press).

C. Light Activation

The antimicrobial effect of the conjugates is activated by exposure to a light source. In one embodiment, the conjugates may be exposed to a light source comprising radiation having a wavelength, or a range of wavelengths, within the range of wavelengths absorbed by the conjugated photosensitiser, preferably near or corresponding to the wavelength of maximum absorption of the photosensitiser ($\lambda_{max}$). In one embodiment, it is preferred that the conjugate demonstrates antimicrobial activity when exposed to visible light, i.e. $\lambda_{max}$ is between about 380 and about 780 nm.

In general, any light source that emits light of an appropriate wavelength may be used. The source of light may be any device or biological system able to generate monochromatic or polychromatic light, coherent or incoherent light, especially visible white light. Examples include a fluorescent light source, laser, one or more light emitting diodes (LEDs), arc lamp, halogen lamp, incandescent lamp or an emitter of bioluminescence or chemiluminescence. In certain circumstances, sunlight may be suitable. Preferably, the wavelength of the light emitted by the light source may be from about 200 to about 1060 nm, preferably from about 380 to about 780 nm. A suitable laser may have a power of from about 1 to about 100 W. Other suitable lasers may have a power of about 1 to about 1000 mW and a beam diameter of from about 1 to about 10 mm. The light dose for laser irradiation is suitably from about 5 to about 333 J cm$^{-2}$, preferably from about 5 to about 30 J cm$^{-2}$ for laser light. For white light irradiation, a suitable dose is from about 0.01 to about 100 J/cm$^2$, preferably from about 0.1 to about 20 J/cm$^2$, more preferably from about 3 to about 10 J/cm$^2$. In a preferred embodiment, the mixture may suitably be irradiated using a source of white light.

Without limitations, the following are examples of light sources and their respective exemplary wavelengths and/or power outputs that may be suitable for use in the present invention:

Helium neon (HeNe) gas laser (e.g. 633 nm, 35 mW output)
Argon-pumped dye laser (e.g. 500-700 nm, 5 W output)
Copper vapour-pumped dye laser (e.g. 600-800 nm)
Excimer-pumped dye laser (e.g. 400-700 nm)
Gold vapour laser (e.g. 628 nm, 10 W output)
Tunable solid state laser (e.g. 532-1060 nm), including Sd:YAG
Light emitting diode (LED) (e.g. 400-800 nm)
Diode laser (e.g. 630-850 nm, 25 W output), e.g. gallium selenium arsenide
Tungsten filament lamp
Halogen cold light source
Fluorescent lamp (e.g. 10 to 30 W)

The present invention is not limited to the above-mentioned examples of light sources, exemplary wavelengths and/or power outputs. It is entirely possible for the present invention to be carried out using other light sources and/or the above-mentioned light sources with different wavelengths and/or power outputs. The duration of exposure to the light source should be long enough to ensure sufficient killing of the microbes. This may vary depending on the choice of photosensitiser and light source. For example, TBO-containing conjugates may require exposure for between about 30 and about 45 minutes to ensure effective killing of microbes using a 15 to 30 W fluorescent lamp, but only about 1 to about 5 minutes using a HeNe laser. In another embodiment, for example when the light source is of low intensity such as exposure to natural daylight, the conjugate is exposed to the light source for a longer period of time, such as for several hours, for example from about 1 to about 12 hours.

The light may be delivered to the conjugate by ambient exposure, or, if necessary or convenient, by use of a directed means such as a fibre optic light source or other known optical devices.

D. Antimicrobial Effect

When used as light activated antimicrobials, the conjugates as described herein are capable of killing or inhibiting the growth of microorganisms, including bacteria, viruses, fungi, protoctists and prions, that can cause disease in humans, animals or plants.

The efficacy of the conjugates as antimicrobials depends on many factors. The choice of nanoparticle type, choice of photosensitiser, nanoparticle size, ratio of nanoparticle:ligand:photosensitiser, concentration of photosensitiser, light source and duration of exposure to light may all influence antimicrobial activity. The skilled person can readily determine suitable combinations.

E. Medical Applications

In one embodiment, the present invention provides conjugates as defined herein for use in treating a human or animal body by administering an effective non-toxic amount of said conjugate, followed by exposure to a suitable light source. In particular, the present invention provides the conjugates for use in killing or preventing the growth of microbes, or for ameliorating or reducing the incidence of proliferative cell disorders such as cancer in the human or animal body. The present invention also provides use of conjugates as described herein in the manufacture of a medicament for killing or preventing the growth of microbes, and a method of treating a human or animal body, which method comprises the administration of an effective non-toxic amount of a conjugate as described herein, followed by exposure to a suitable light source.

In one embodiment, the conjugates of the present invention are used to kill or inhibit the growth of *Staphylococcus aureus*. The conjugates of the present invention may also be used to kill or inhibit the growth of *Propionibacterium acnes* and the microbes involved in oral diseases, such as inflammatory periodontal disease and caries, or in infections at other body sites. For example, the conjugates of the present invention may also be used to kill or inhibit the growth of *Streptococcus sanguis, Porphyromonas gingivalis, Fusobacterium nulceatum, Actinobacillus actinomycetemcomitans, Candida albicans, Streptococcus mutans, Streptococcus pyogenes, Pseudomonas aeruginaosa, Escherichia Coli* and lactobacilli.

If the conjugate comprises a targeting moiety, this may bind to the microbes of interest, enhancing the antimicrobial effect. When the nanoparticle of such a targeted conjugate comprises core-shell particles having a magnetic core, it may be possible to remove the conjugates, before or after the step of exposure to a light source, by using a magnetic field. Such a step would also remove microbes attached to the conjugate via the targeting moiety, thereby "cleaning" the treated site. Such an application could be particularly advantageous when the treated site is a wound.

Conjugates comprising targeting moieties could also be advantageous in treating, ameliorating or reducing the incidence of proliferative cell disorders such as cancer. Thus the present invention also provides a method of treating proliferative cell disorders such as cancer, which method comprises the administration of an effective non-toxic amount of a conjugate as described herein comprising a suitable targeting moiety, followed by exposure to a light source. Suitable light sources for treatment of cancerous tumours have wavelengths in the near infrared (NIR) region, e.g. from about 800 to about 1600 nm. Thus, conjugates should be chosen such that they are active at such wavelengths: in particular, the photosensitiser may be chosen such that it absorbs in such a wavelength range.

In one embodiment, the conjugates as described herein are for use in systemic or topical applications. For example, the conjugates may be applied topically to skin, wounds or a mucosal surface in order to kill or inhibit the growth of microbes thereon. As a further example, the conjugates of the present invention may find application in killing or preventing the growth of fungi, for example in infections of the nail bed. Alternatively, they may be used systemically to kill or prevent the growth of microbes within body tissues.

Such treatment of systemic infections may also be achieved outside the body. For example, the present invention may comprise a method for killing or preventing the growth of microbes in a fluid such as blood, comprising adding a conjugate as described herein to the fluid followed by exposure to a suitable light source.

The fluid containing the conjugate may be flowed into and through a photopermeable container for irradiation, using a flow through type system. Alternatively, the fluid to be treated may be placed in a photopermeable container which is agitated and exposed to the light source for a time sufficient to substantially inactivate the microbes, in a batch-wise type system. Any suitable apparatus may be used for such a procedure, for example a radiation or treatment chamber. Suitable containers include bags, boxes, troughs, tubes or tubing. Batch-wise treatment of the fluid may be achieved using, for example, collection bags. Preferably, the container is agitated during treatment to mix the fluid and conjugate and ensure that the majority of the fluid is exposed to the light source. Continuous treatment may be achieved via an extracorporeal loop, wherein blood is contacted with the conjugate and exposed to a light source whilst in the loop.

The light source may be continuous or pulsed. The conjugate may be added directly to the fluid to be treated, or may be flowed into the photopermeable container separately from the fluid being treated, or may be added to the fluid prior to placing the fluid in the photopermeable treatment container. The conjugate may also be added to the photopermeable container either before or after sterilization of the treatment container.

The present invention also provides a method of disinfecting or sterilising a locus in a patient, which method comprises the administration to the said locus of an effective non-toxic amount of a conjugate as described herein followed by exposure of said locus to a suitable light source.

The conjugates as described herein may be for use in killing or preventing the growth of microbes in a body cavity. As noted above, body cavity shall mean any cavity within a body such as mouth or oral cavity, nose, ear, vagina, lung, the entire digestive tract (e.g., throat, esophagus, stomach, intestines, rectum, etc.), gall bladder, bladder, any open wound or the like. The body cavity can be within a human body or a body of another animal. In a preferred aspect the invention provides the use of conjugates as described herein in the manufacture of a medicament for use in disinfecting or sterilising tissues of a body cavity or a wound or lesion in a body cavity by (a) contacting the tissues, wound or lesion with conjugates and (b) irradiating the tissues, wound or lesion with a suitable light source.

The wound or lesion treated may be any surgical or trauma-induced wound, a lesion caused by a disease-related microbe, or a wound or lesion infected with such a microbe. The treatment may be applied to disinfect or sterilise a wound or lesion as a routine precaution against infection or as a specific treatment of an already diagnosed infection of a wound or lesion. In one embodiment, the body cavity is the oral cavity.

The conjugates of the present invention may also be used in other body cavities, such as the nose, rectum, bladder, lungs, vagina, etc.

In another preferred aspect the invention provides the use of conjugates of the present invention in the manufacture of a medicament for use in killing or preventing the growth of disease-related microbes in a body cavity, such as the oral cavity, nose, rectum, bladder, lungs, vagina, etc. by (a) contacting the microbes with conjugates and (b) irradiating the microbes with a suitable light source.

In another embodiment, the conjugates as described herein are for use in killing or inhibiting the growth of the microbes involved in oral diseases. Thus, when the body cavity is the oral cavity, the treatment with conjugates and irradiation are preferably applied to (i) destruction of disease-related microbes in a periodontal pocket in order to treat chronic periodontitis; (ii) destruction of disease-related microbes in the region between the tooth and gingiva (gingival crevice or gingival margin) in order to treat or prevent inflammatory periodontal diseases, including chronic periodontitis, gingivitis and the like; (iii) disinfection or sterilisation of drilled-out carious lesions prior to filling; (iv) destruction of cariogenic microbes on a tooth surface in order to prevent dental caries; (v) disinfection or sterilisation of dental and/or gingival tissues in other dental surgical procedures and (vi) treatment of oral candidiasis in AIDS patients, immunocompromised patients or patients with denture stomatitis.

For such applications, the conjugates are suitably in the form of a solution or a suspension in a pharmaceutically acceptable aqueous carrier, but may be in the form of a solid such as a powder or a gel, an ointment or a cream. The pharmaceutical composition may further comprise one or more accessory ingredients selected from buffers, salts for adjusting the tonicity of the solution, antioxidants, preservatives, gelling agents and remineralisation agents. The composition may be applied to the infected area by painting, spreading, spraying, injecting or any other conventional technique, in order to contact the conjugate with the microbes.

The conjugate may be left in contact with the microbes for a period of time. The duration of time may vary depending on the particular photosensitiser in use and the target microbes to be killed. For example, it can be from about 1 second to about 10 minutes. In one embodiment, the duration of time is about 10 seconds to about 2 minutes. In another embodiment, the duration of time is about 30 seconds.

F. Non-Medical Applications

In one aspect, the present invention does not extend to the use of the mixtures in methods for treatment of the human or animal body by surgery or therapy, or in diagnostic methods practised on the human or animal body.

The conjugates of the present invention may be used to kill or inhibit the growth of microorganisms on inanimate objects or surfaces. In one embodiment, the conjugates of the present invention are used to kill or inhibit the growth of *Staphylococcus aureus*.

The antimicrobial properties of the conjugates of the present invention may find application in hospitals and other places where microbiological cleanliness is necessary, for example food processing facilities, dining areas or play areas. Use in abattoirs is also envisaged. The conjugates may be applied to any suitable surface in order to sterilize or disinfect it, for example work surfaces, wash basins, toilets, tiles, door handles or computer keyboards. In another embodiment, the conjugates may be applied to cling-film or other films or packaging, such as food packaging, for example by spraying or painting a solution of the conjugate onto the film. Such antimicrobial films or packaging could also be produced by incorporating the conjugate into the film/packaging. The cling-film type material could be wrapped around or used to cover medical/dental instruments, computer input devices, food or drink products, surfaces etc.

The conjugates may be applied as a coating by painting, spreading or spraying and may be dried or allowed to dry naturally. They can also be mixed with a plastics material such as cellulose acetate to create an antimicrobial plastic. Such a plastics material could be used to manufacture articles, such as computer input devices, or as antimicrobial coverings to be wrapped or coated over the surface of the article to be treated. Thus, in one embodiment, an article such as a computer input device could be coated with a mixture of cellulose acetate and the conjugate.

In another embodiment, the conjugates of the present invention may be used to sterilise or disinfect textiles or fabrics. For example, the conjugates may be applied to articles such as clothes, bed sheets, lab coats, curtains or furniture. Application may be effected by, for example, spraying or otherwise applying a suitable solution/suspension containing the conjugates, or soaking in such a solution/suspension. The article may then be exposed to a suitable light source for a sufficient amount of time to kill or prevent the growth of microbes in or on the article.

In another embodiment, the conjugates of the present invention may be used to sterilise or disinfect fluids, such as water. The present invention may therefore comprise a method for killing or preventing the growth of microbes in a fluid, such as water, comprising adding a conjugate as described herein to the fluid followed by exposure to a suitable light source. The conjugate may comprise core-shell particles having a magnetic core, so that it may be possible to remove the conjugates by using a magnetic field, as described above. Such conjugates comprising magnetic particles may also comprise a targeting moiety, which may bind to the microbes, enhancing the antimicrobial effect and enabling the microbes to be removed along with the conjugate.

In a further embodiment, the conjugates of the present invention may be applied to plants in order to control plant pests or pathogens such as fungi, bacteria or viruses. After application of the conjugate, for example by spraying, the plant may be exposed to a suitable light source for a sufficient amount of time to kill or prevent the growth of plant pests or pathogens. Sunlight may be such a suitable source. In one embodiment, the conjugates of the present invention are applied to non-edible plants.

The present invention also provides a process of killing or preventing the growth of microbes on an inanimate object or surface, comprising contacting with a conjugate according to the present invention followed by exposure to a light source for a sufficient amount of time to kill or prevent the growth of microbes. Suitable light sources are described above. As described above, the mixture is at a suitable concentration such that a desired level of antimicrobial activity is achieved at the treatment site. For application to surfaces, the mixture may be applied directly by any suitable means, such as a cloth, spray or wash.

The conjugate may be left in contact with the microbes for a period of time, such as those described above for medical applications.

III. Examples

Please note that these examples are for the purpose of illustration only and are not to be construed as limiting the scope of the invention in any way.

Example 1

Gold nanoparticles (2.0 nm diameter; British Biocell International) in water ($15 \times 10^{13}$ particles per ml) were mixed with an equal volume of an aqueous solution of toluidine blue O (40 μM) and left at room temperature for 15 minutes. 100 μl of the gold-TB solution was added to 100 μl of a suspension of *Staphylococcus aureus* NCTC 6571 in phosphate buffered saline (PBS) and this was irradiated with white light from a fluorescent white lamp for 10 minutes. Controls consisted of:

(i) TB (final concentration=10 μM) and bacteria, irradiated for the same period of time, (ii) nanogold (diluted 1:1 with water) and bacteria, irradiated for the same period of time, (iii) bacteria without TB or nanogold, not irradiated ("control").

After irradiation, the number of surviving bacteria was determined by viable counting. The results of the experiments (carried out twice with duplicate counts on each occasion) are shown in Table 1. The gold nanoparticles alone when irradiated did not achieve significant killing of the bacteria. The TB-gold achieved approximately a one log greater kill than the TB alone −99.3% kill as opposed to a 93.7% kill. Note that the TB concentration and light energy dose used were designed to give sub-optimal kills so that differences in efficacy of the TB and the TB-nanogold could be discerned. Preliminary experiments using 30 minutes light exposure achieved total kills of the bacterial suspensions in both cases.

TABLE 1

| Sample[1] | *S. aureus* (cfu/ml) | % Kill |
| --- | --- | --- |
| Control | 135000000 | — |
| Gold only | 81000000 | 40.0 |
| TB only | 8570000 | 93.7 |
| Mixture (L + TB + G+) | 983000 | 99.3 |

[1]Samples were irradiated with light from a 28 W fluorescent white lamp. US application number 60/821,423 mentions an 18 W lamp.

Example 2

Production of Water-Soluble Gold Nanoparticles $HAuCl_4.3H_2O$ (42 mg, 0.11 mmol) was dissolved in deionised water (25 ml) to form solution A ~5 mM). $Na_3C_6H_5O_7.2H_2O$ (125 mg, 0.43 mmol) was dissolved in deionised water (25 ml) to give solution B (~20 mM). Solution A (1 ml) was stirred with deionised water (18 ml) and boiled for 2 min. Then solution B (1 ml) was added dropwise over a period of approximately 50 sec. causing the colour change from clear to blue to pink/purple. After a further 1 min. of heating, the solution was left to cool to room temperature. Two batches of nanogold particles were used for subsequent antibacterial assays—these are designated NN1 and NN2. The absorption spectrum of NN2 showed the wavelength of maximum absorption, $\lambda_{max}$, to be 527 nm. Batch NN1 had a $\lambda_{max}$ of 522 nm. Particle size analysis (position of UV plasmon absorption band measured using transmission electron microscope) of batch NN1 gave an average diameter of 14.76±2.34 nm.

Effect of Concentration of Photosensitiser

Gold nanoparticles of approximately 15 nm in diameter (batches NN1 and NN2 above) were mixed with an equal volume of aqueous toluidine blue O (TB) and left at room temperature for 15 minutes. TB was used at a final concentration of 1, 5, 10, 20 or 50 µM. 100 µl of the TB-gold mixture was added to 100 µl of a suspension of *Staphylococcus aureus* NCTC 6571 in phosphate buffered saline (PBS) (adjusted to an optical density of 0.05), and samples were irradiated with a fluorescent white light (28 W) for 10 minutes. *S. aureus*+TB only, and *S. aureus*+PBS, without photosensitiser or nanogold were used as controls. The final concentration of nanogold used was $1 \times 10^{15}$ particles/ml. After irradiation, the numbers of surviving bacteria were enumerated by viable counting. The results are shown in Table 2 below.

In the case of the 15 nm nanogold, there was little enhancement of lethal photosensitisation (compared with that achieved when TB was used in the absence of nanogold) when the TB concentration was 1 µM whereas enhancement was evident using higher TB concentrations of 5, 10 and 20µ. Enhancement was greatest using 10 and 20 µM TB. Enhancement appears to be dependent on the ratio of TB to nanogold. There was little enhancement of lethal photosensitisation when the TB concentration was 10 or 100 µM, whereas enhancement was greatest using TB concentrations of 20 and 50 µM.

Example 3

The method of Example 2 was repeated using gold nanoparticles of 2 nm diameter (British Biocell International). The final concentration of nanogold used was $4 \times 10^{13}$ particles/ml. TB was used at a final concentration of 10, 20 or 50 µM. The results are shown in Table 2 below. When the 2 nm nanogold particles were used, enhancement of lethal photosensitisation was evident using 20 µM TB but not when either 10 µM or 50 µM TB was used.

Example 4

Effect of Concentration of Gold Nanoparticles

Experiments were performed as for Example 3, with the following modifications. Prior to mixing with the photosensitiser, the gold nanoparticles were either left undiluted, or diluted 1 in 10 or 1 in 100 in sterile, distilled water. The nanoparticles were then added to TB (final concentration 20 µM). The samples were then illuminated for 30 seconds using a fibre optic white light source (Schott KL200). The surviving bacteria were enumerated by viable counting as before. The results are shown in Table 2 below. When the nanoparticles were diluted 1 in 10 a greater enhancement was achieved compared with that obtained using undiluted nanogold.

Example 5

Example 4 was repeated using methylene blue (MB; 20 µM) as the photosensitiser. The results are shown in Table 2 below. The enhancement achieved by the nanogold with a larger particle size (15 nm) was not increased when the nanogold concentration was decreased.

Example 6

Example 5 was repeated using 2 nm gold nanoparticles (British Biocell International). The results are shown in Table 2 below. Diluting the 2 nm gold nanoparticles enhanced the killing of *S. aureus* slightly when used in combination with methylene blue.

Example 7

Example 6 was repeated using tin chlorin e6 (SnCe6; 20 µg/ml) as the photosensitiser. The illumination time was 10 minutes. The results are shown in Table 2 below. Diluting the 2 nm gold nanoparticles enhanced the killing of *S. aureus* when used in combination with tin chlorin e6.

Example 8

Example 3 was repeated using nile blue sulphate as the photosensitiser. Samples were illuminated for 30 minutes. The results are shown in Table 2 below.

TABLE 2

| Example | Photosensitiser | Concentration of photosensitiser[1] (µM) | Nanoparticle size (nm) | Nanoparticle concentration[1] (particles/ml) | Result[2] |
|---|---|---|---|---|---|
| 2 | Toluidine blue | 1 | 15 | $1 \times 10^{15}$ | — |
|   |   | 5 |   |   | * |
|   |   | 10 |   |   | /* |
|   |   | 20 |   |   | **** |
|   |   | 50 |   |   | **** |
|   |   | 100 |   |   | ** |
| 3 | Toluidine blue | 10 | 2 | $4 \times 10^{13}$ | * |
|   |   | 20 |   |   | **** |
|   |   | 50 |   |   | * |
| 4 | Toluidine blue | 20 | 15 | $1 \times 10^{15}$ | *** |
|   |   |   |   | $1 \times 10^{14}$ | **** |
| 5 | Methylene blue | 20 | 15 | $1 \times 10^{15}$ | **** |
|   |   |   |   | $1 \times 10^{14}$ | **** |
|   |   |   |   | $1 \times 10^{13}$ | **** |
| 6 | Methylene blue | 20 | 2 | $4 \times 10^{13}$ | **** |
|   |   |   |   | $4 \times 10^{12}$ | **** |
|   |   |   |   | $4 \times 10^{11}$ | **** |
| 7 | Tin chlorine6 | 20[3] | 2 | $4 \times 10^{13}$ | — |
|   |   |   |   | $4 \times 10^{12}$ | ** |
|   |   |   |   | $4 \times 10^{11}$ | *** |
| 8 | Nile blue sulphate | 10 | 2 | $4 \times 10^{13}$ | *** |
|   |   | 20 |   |   | **** |
|   |   | 50 |   |   | **** |

[1] concentration in mixed solution
[2] Key: — less than 50% kill; * 50-90% kill;  90-95% kill; * 95-99% kill; **** 99-100% kill
[3] concentration in µ/ml

Example 9

Synthesis of TBO-Tiopronin-Gold Nanoparticle Conjugates

Chemicals: Hydrogen tetrachloroaurate (tetrachloroauric acid; $HAuCl_4.3H_2O$, 99.99%), N-(2-mercaptopropionyl)glycine (tiopronin, 99%) and sodium borohydride (99%) were purchased from Aldrich. Toluidine Blue O ("TBO", 90%) was purchased from Acros Organics. Buffers were prepared according to standard laboratory procedure. All other chemicals were reagent grade and used as received. The synthesis of the conjugates involved two steps:
(1) Synthesis of tiopronin-gold nanoparticle conjugate; and
(2) Preparation of TBO-tiopronin-gold nanoparticle conjugate.

Synthesis of Tiopronin-Gold Nanoparticle Conjugate:

Tetrachloroauric acid (0.62 g; 1.57 mmol) and N-(2 mercaptopropionyl) glycine (tiopronin, 0.77 g; 4.72 mmol) were dissolved in 6:1 methanol/acetic acid (70 mL) giving a ruby red solution. Sodium borohydride ($NaBH_4$, 1.21 g; 32 mmol) in water (30 mL) was added with rapid stirring, whereupon the solution temperature immediately rose from 24° C. (room temperature) to 44° C. (returning to room temperature in ca. 15 min). Meanwhile, the solution pH increased from its initial 1.2 value to 5.1. The black suspension that was formed was stirred for an additional 30 min after cooling, and the solvent was then removed under vacuum at <40° C.

The crude reaction product was completely insoluble in methanol but quite soluble in water. It was purified by dialysis, in which the pH of the crude product dissolved in water (80 mL) was adjusted to 1 by dropwise addition of concentrated hydrochloric acid (HCl). This solution was loaded into 20 cm segments of cellulose ester dialysis membrane (Spectra/Por CE, MWCO=12000), placed in a 4 L beaker of water, and stirred slowly, recharging with fresh water ca. every 12 hours over the course of 72 hours. The dark tiopronin-gold nanoparticle conjugate solution was collected from the dialysis tube, and the solvent was removed by freeze-drying. The product materials were found to be spectroscopically clean ($^1$H NMR in $D_2O$, 10 mg of sample: absence of signals due to unreacted thiol or disulfide and acetate byproducts). Elemental analysis of the dialysed tiopronin-gold nanoparticle conjugate gave the following. Anal. Found: C, 11.70; H, 1.65; N, 2.55; S, 5.73. Calcd for $C_{425}H_{680}O_{255}N_{85}S_{85}Au_{201}$: C, 9.56; H, 1.28; N, 2.23; O, 7.65; S, 5.11; Au, 74.17.

Preparation of TBO-Tiopronin-Gold Nanoparticle Conjugate

Tiopronin-gold nanoparticle conjugates (MW=53376.38 g/mol, 100 mg, 1.87 µmol) were dissolved in 50 mM 2-(N-morpholino)ethanesulfonic acid (MES) buffer (pH 6.5; 30 mL) and the solution then made up to 0.1 M in 1-[3-(dimethylamino)-propyl]-3-ethylcarbodiimide hydrochloride (EDC) and 5.31 mM in N-hydroxysulfosuccinimide sodium salt. Toluidine Blue 0 (TBO, 61 mg, 0.2 mmol) was added, and the solution was stirred for 24 hours. Then, the reaction mixture was dialyzed as described above for 144 hours. The dark purple TBO-tiopronin-gold nanoparticle conjugate solution was collected from the dialysis tube, and the solvent was removed by freeze-drying. $^1$H NMR spectroscopy (in $D_2O$/phosphate buffer-d; 8 mg of sample) revealed pure product. The number of molecules of TBO coupled to each nanoparticle was 15.4, as determined by $^1$H NMR. This value was verified by elemental analysis. Anal. Found: C, 14.45; H, 1.91; Cl, 0.86; N, 3.35; S, 5.58. Calcd for $C_{656}H_{895.6}Cl_{115.4}O_{239.6}N_{131.2}S_{100.4}Au_{201}$: C, 13.63; H, 1.56; Cl, 0.94; N, 3.18; 0, 6.63; S, 5.57; Au, 68.49.

The following Examples 10-13 deal with lethal photosensitisation of *Staphylococcus aureus* using a TBO-tiopronin-gold nanoparticle conjugate.

Example 10

White Light

An overnight culture of *Staphylococcus aureus* NCTC 6571 (1 ml; grown aerobically at 37° C., with shaking, in Nutrient Broth no. 2) was centrifuged and the pellet resuspended in phosphate buffered saline ("PBS", 1 ml). The optical density at 600 nm was adjusted to 0.05 in PBS, in order to give an inoculum of approximately $10^7$-$10^8$ cfu/ml. A TBO-tiopronin-gold nanoparticle conjugate, prepared by a method analogous to that described in Example 9, approximate composition $Au_{201}tiopronin_{85}TBO_{11}$, was suspended in sterile distilled water at a concentration of 4.6 mg/ml. The conjugate solution was then diluted 1 in 2, 1 in 10 and 1 in 100 in sterile distilled water. In a 96-well plate, 50 µl aliquots of the conjugate were added to 50 µl of the bacterial suspension, in triplicate, and irradiated with white light (28 W compact fluorescent lamp; 3600±20 lux) for 35 minutes. Controls consisted of:

(i) bacteria without conjugate, kept in the dark for an equal amount of time ("control");

(ii) bacteria with conjugate, kept in the dark for an equal amount of time;

(iii) irradiated tiopronin-gold nanoparticle conjugate with free TBO; and (iv) irradiated tiopronin-gold nanoparticle conjugate alone.

After irradiation, samples were serially diluted 1 in 10 to a dilution factor of $10^{-4}$ and spread in duplicate onto 5% horse blood agar plates. The plates were then incubated aerobically at 37° C. for approximately 48 hours. After incubation, the surviving cfu/ml was calculated. The results are summarised in Table 3. The conjugate had no effect when irradiated with white light for 35 minutes when used neat or at a dilution of 1 in 2, and little effect at a dilution of 1 in 100. However, antibacterial activity (approximately 4 log reduction in colony forming units/ml) was observed when the conjugate was diluted 1 in 10.

The absence of killing by the undiluted and 1 in 2 dilutions of the conjugate were likely to be due to light absorption by the very darkly coloured solutions. The small kills detected using a 1 in 100 dilution were probably due to the very low concentrations of TBO present. When not exposed to white light, no antibacterial activity was seen at any concentration of the conjugate tested. Furthermore, neither free TBO in combination with the tiopronin-gold nanoparticles, nor the tiopronin-gold nanoparticles alone achieved any killing of *S. aureus* 6571 at any of the concentrations tested.

Example 11

HeNe Laser

The method of Example 10 was repeated using a helium-neon laser (power output=35 mW; emitting light at 632 nm) instead of white light, with an irradiation time of one minute. The results are shown in Table 3. As with the white light, the concentration that achieved the best killing of *S. aureus* was a 1 in 10 dilution. However in contrast to the results using the white light; antibacterial activity (approximately 2 log reduction in cfu/ml) was also observed when the conjugate was diluted 1 in 2.

Example 12

Effect of Light Dose (White Light)

The method of Example 10 was repeated, using TBO-Tiopronin-gold nanoparticle conjugate at 1 in 10 dilution. Samples were illuminated with the same white light source as described above for 15, 30, or 45 minutes. Results are shown in Table 3. No antibacterial effect was observed after 15 minutes. The conjugate achieved approximately a two log reduction in the surviving cfu/ml after 30 minutes irradiation, increasing to an approximately 5 log reduction in cfu/ml after 45 minutes. The effect of TBO alone was also investigated, and was found to have no effect when irradiated with white light for any length of time.

Example 13

Effect of Light Dose (HeNe Laser)

The method of Example 12 was repeated, but samples were irradiated with the HeNe laser described in Example 3 for 0.5, 1, 1.5, 2 or 5 min. Results are shown in Table 3. This was then repeated with irradiation for one, two or five minutes. Highly effective killing was achieved for exposure times of 1 min and above. As seen with white light, the results showed a dose response, in which killing of *S. aureus* increased with increased irradiation time, with most killing being seen at five minutes (approximately 5.5 log reduction in cfu/ml).

TABLE 3

| Example | Light Source | Irradiation time (min) | Dilution of conjugate solution[1] | Result[2] |
|---|---|---|---|---|
| 10 | White | 35 | Neat | — |
|  |  |  | 1 in 2 | — |
|  |  |  | 1 in 10 | **** |
|  |  |  | 1 in 100 | ** |
| 11 | HeNe laser | 1 | Neat | — |
|  |  |  | 1 in 2 | **** |
|  |  |  | 1 in 10 | **** |
|  |  |  | 1 in 100 | * |
| 12 | White | 15 | 1 in 10 | — |
|  |  | 30 |  | **** |
|  |  | 45 |  | **** |
| 13 | HeNe laser | 0.5 | 1 in 10 | *** |
|  |  | 1 |  | **** |
|  |  | 1.5 |  | **** |
|  |  | 2 |  | **** |
|  |  | 5 |  | **** |

[1]Before mixing with bacterial suspension
[2]Key: - less than 50% kill; * 50-90% kill;  90-95% kill; * 95-99% kill; **** 99-100% kill Examples 14-15 deal with lethal photosensitisation of *Staphylococcus aureus* using a different TBO-tiopronin-gold nanoparticle conjugate.

Example 14

White Light

An overnight culture of *Staphylococcus aureus* NCTC 6571 (1 ml; grown aerobically at 37° C., with shaking, in Nutrient Broth no. 2) was centrifuged and the pellet resuspended in phosphate buffered saline ("PBS", 1 ml). The optical density at 600 nm was adjusted to 0.05 in PBS, in order to give an inoculum of approximately $10^7$-$10^8$ cfu/ml. The TBO-tiopronin-gold nanoparticle conjugate prepared in Example 9, approximate composition $Au_{201}tiopronin_{85}TBO_{15.4}$, was suspended in PBS at a concentration of 4.6 mg/ml, such that the final TBO content was approximately 1 mM. The conjugate solution was then diluted in PBS to give final TBO concentrations of approximately 2 µM, 1.0 µM, 0.5 µM and 0.25 µM. In a 96-well plate, 50 µl aliquots of the conjugate were added to 50 µl of the bacterial suspension, in triplicate, and irradiated with white light (28 W compact fluorescent lamp; 3600±20 lux) for 30 minutes. Controls consisted of:

(i) bacteria without conjugate;

(ii) TBO;

(iii) irradiated tiopronin-gold nanoparticle conjugate with free TBO at a final TBO concentration of 1 µM; and (iv) irradiated tiopronin-gold nanoparticle conjugate alone: it was calculated that prior to dilution, the TBO-tiopronin-gold nanoparticle conjugate contained approximately 81 µM tiopronin-gold, and therefore a stock solution of the tiopronin-gold nanoparticle conjugate was made up to this concentration and then diluted accordingly.

After irradiation, samples were serially diluted 1 in 10 to a dilution factor of $10^{-4}$ and spread in duplicate onto 5% horse blood agar plates. The plates were then incubated aerobically at 37° C. for approximately 48 hours. After incubation, the surviving cfu/ml was calculated. The results are shown in FIG. 1 and summarised in Table 4. FIG. 1 shows the effect of TBO and the TBO-tiopronin-gold nanoparticle conjugate on viability of *Staphylococcus aureus* 6571 following exposure to white light for 30 minutes, or incubation in the dark with TBO or the TBO-tiopronin-gold nanoparticle conjugate. The white bar in FIG. 1 denotes the viable count of the original bacterial suspension, and the dotted bar represents the viable count of the bacterial suspension after exposure to white light alone. There was a concentration-dependent reduction in the viable count of *S. aureus* on irradiation with white light for 30 mins. At a concentration of 2.0 µm, an approximately 5.5 $log_{10}$ reduction in the viable count was observed. Substantial kills were achieved using a conjugate concentration as low as 0.5 µm, whereas free TBO exhibited significant kills of the organism only at a concentration of 2.0 µm. The TBO-free tiopronin-gold nanoparticles did not achieve any killing of *S. aureus* 6571 at any of the concentrations tested. Mixtures of various ratios of the tiopronin-gold conjugate and a suboptimal concentration of TBO (1.0 µM) did not result in killing of the *S. aureus* on irradiation with white light.

Example 15

HeNe Laser

Figure 2:
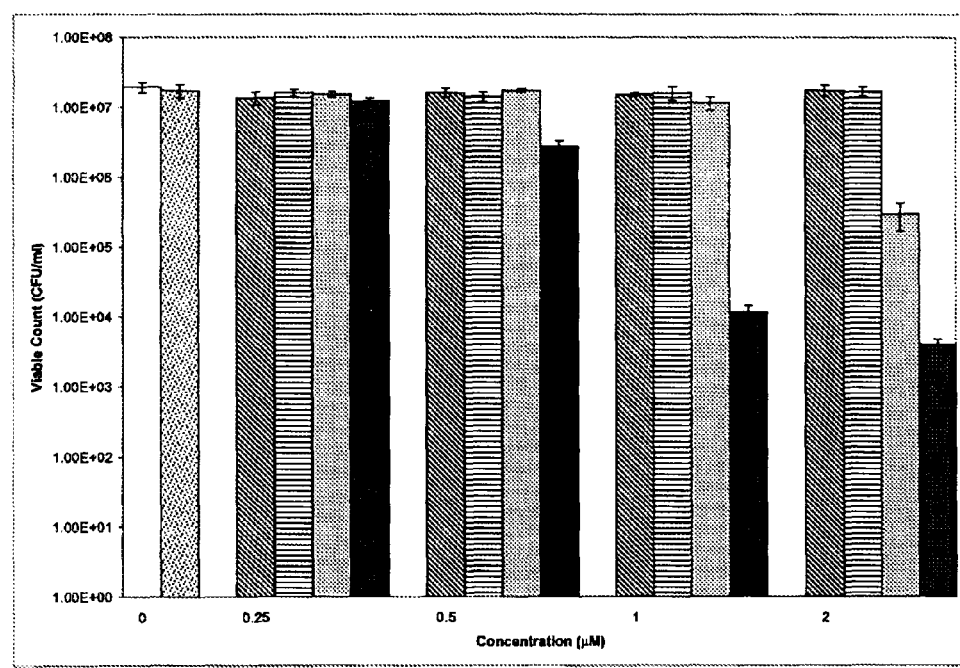
FIG. 2 shows the effect of TBO and the TBO-tiopronin-gold nanoparticle conjugate on viability of S. aureus 6571 following exposure to HeNe laser light for 1 minute, or incubation in the dark with TBO or the TBO-tiopronin-gold nanoparticle conjugate.

The method of Example 14 was repeated using a helium-neon laser (power output=35 mW, emitting light at 632 nm) instead of white light with an irradiation time of one minute. The results are shown in FIG. 2 and Table 4. FIG. 2 shows the effect of TBO and the TBO-tiopronin-gold nanoparticle conjugate on viability of *S. aureus* 6571 following exposure to HeNe laser light for 1 minute, or incubation in the dark with TBO or the TBO-tiopronin-gold nanoparticle conjugate. The white bar in FIG. 2 denotes the viable count of the original bacterial suspension, and the dotted bar represents the viable count of the bacterial suspension after exposure to HeNe laser light alone. As with the white light, the kills achieved were concentration-dependent—significant kills were achieved when the conjugate was used at a concentration as low as 0.5 µM.

TABLE 4

| Example | Light Source | Irradiation time (min) | TBO concentration (μM) | Result[1] |
|---|---|---|---|---|
| 14 | White | 30 | 2.0 | **** |
| | | | 1.0 | **** |
| | | | 0.5 | **** |
| | | | 0.25 | * |
| 15 | HeNe laser | 1 | 2.0 | **** |
| | | | 1.0 | **** |
| | | | 0.5 | * |
| | | | 0.25 | — |

[1]Key: - less than 50% kill; * 50-90% kill;  90-95% kill; * 95-99% kill; **** 99-100% kill.

The preferred embodiments of the present invention have been disclosed. A person of ordinary skill in the art would realize however, that certain modifications would come within the teachings of this invention. Therefore, the following claims should be studied to determine the true scope and content of the invention.

The invention claimed is:

1. A composition comprising charge-stabilized metallic nanoparticles and a photosensitiser, wherein the metallic nanoparticles are gold nanoparticles and wherein the photosensitiser is selected from phenothiaziniums, dihaematoporphyrin ester, tin chlorin e6, porfimer sodium, and a combination thereof, the concentration of photosensitiser in the composition is from about 5 to about 100 μM, and wherein the composition is mixed with a plastic material.

2. The composition of claim 1, wherein the nanoparticles have a diameter of from about 1 nm to about 30 nm.

3. The composition of claim 1, wherein the photosensitiser is selected from a group consisting of toluidine blue O, methylene blue, dihaematoporphyrin ester, tin chlorin e6, porfimer sodium, and a combination thereof.

4. The composition of claim 1, wherein the photosensitiser is methylene blue.

5. The composition of claim 1, wherein the photosensitizer is toluidine blue O.

6. The composition of claim 1, wherein the concentration of the nanoparticles in the mixture is from about $1 \times 10^{11}$ to about $5 \times 10^{15}$ particles/ml.

7. The composition of claim 1, wherein the composition further comprises crystal violet.

8. The composition of claim 4, wherein the composition further comprises crystal violet.

* * * * *